United States Patent [19]

Samreth et al.

[11] Patent Number: 4,960,758
[45] Date of Patent: * Oct. 2, 1990

[54] NOVEL β-D-PHENYLTHIOXYLOSIDES, THEIR METHOD OF PREPARATION AND THEIR USE AS PHARMACEUTICALS

[75] Inventors: Soth Samreth, Longvie; François Bellamy, Saulon la Chapelle; Jean Millet, Saulon la Rue, all of France

[73] Assignee: Fournier Innovation et Synergie, Paris, France

[*] Notice: The portion of the term of this patent subsequent to Oct. 31, 2006 has been disclaimed.

[21] Appl. No.: 266,857

[22] Filed: Nov. 3, 1988

Related U.S. Application Data

[63] Continuation-in-part of Ser. No. 185,422, Apr. 25, 1988, Pat. No. 4,877,808.

[51] Int. Cl.⁵ .................... C07D 335/02; A61K 31/38
[52] U.S. Cl. ..................... 514/24; 514/432; 549/28; 536/41; 536/182; 536/184
[58] Field of Search .................. 549/28; 536/41, 18.2, 536/18.4; 514/432, 24

[56] References Cited

U.S. PATENT DOCUMENTS 3,243,425  3/1966  Whistler et al. ............... 260/210
4,515,782  5/1985  Schaub et al. ................. 514/24

FOREIGN PATENT DOCUMENTS 0051023  5/1982  European Pat. Off. .
0133103  2/1985  European Pat. Off. .

OTHER PUBLICATIONS

Frechet et al., *Journal of the American Chemical Society,* 93:2, pp. 492–496, Jan. 27, 1971.
Chemical Abstracts, vol. 85, No. 25, Abstract 193024x, Dec. 20, 1976, Audichya et al.
Chemical Abstracts, vol. 93, No. 23, Abstract 221016g, Dec. 8, 1980, Ferrier et al.

*Primary Examiner*—Mary G. Lee
*Assistant Examiner*—M. S. Howard
*Attorney, Agent, or Firm*—Fleit, Jacobson, Cohn, Price, Holman & Stern

[57] ABSTRACT

The present invention relates to β-D-phenylthioxyloside compounds selected from the group consisting of:
(i) the β-D-phenylthioxylosides of the formula:

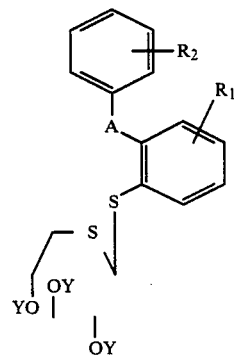

(I)

in which:
R$_1$ and R$_2$, which can be identical or different, which represent a hydrogen atom or a trifluoromethy or cyano group,
A represents CHOH or CO and
Y represents a hydrogen atom or an acyl group; and
(ii) epimers thereof when A is CHOH.

The said β-D-phenylthioxyloside compounds are useful in therapy as antithrombotics.

4 Claims, No Drawings

NOVEL β-D-PHENYLTHIOXYLOSIDES, THEIR METHOD OF PREPARATION AND THEIR USE AS PHARMACEUTICALS

CROSS REFERENCE

The present invention is a continuation-in-part application of prior U.S. patent application Ser. No. 07/185,422 filed on Apr. 25, 1988, now U.S. Pat. No. 4,877,808.

FIELD OF THE INVENTION

The present invention relates, by way of novel industrial products, to the β-D-phenylthioxyloside compounds of formula I below. It further relates to their method of preparation and their use in therapy as antithrombotics, especially venous antithrombotics.

The said prior U.S. patent application related to (i) the β-D-phenylthioxyloside compounds of the para type having the general formula:

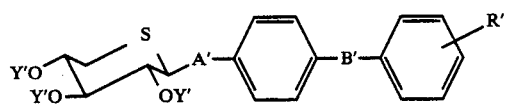

in which:
R' represents a hydrogen atom, a halogen atom, a nitro group or a cyano group,
A' represents the sulfur atom or the oxygen atom,
B' represents a $CH_2$, CHOH or CO group and
Y' represents the hydrogen atom or an acyl group; and (ii) epimers thereof when B' is CHOH.

The present invention relates to analogous compounds of the ortho type which exhibit valuable properties as antithrombotics, especially venous antithrombotics.

PRIOR ART

European patent document No. B-0051023 has already proposed benzoylphenyloside and α-hydroxybenzylphenyloside derivatives as antiulcer agents, platelet aggregation inhibitors, antithrombotics and cerebral oxygenators.

European patent document No. A-0133103 also discloses benzylphenylosides which are useful as hypocholesterolemics and hypolipidemics, some of these compounds, in particular the product of Example 1, having antithrombotic effects as well.

OBJECT OF THE INVENTION

It has now been found that the β-D-phenylthioxyloside compounds according to the invention, which are structurally different from the known products of the prior art, are useful in the treatment and prevention of diseases associated with circulatory disorders, especially as venous antithrombotics.

Unexpectedly, the compounds according to the invention have antithrombotic properties which are greatly superior to those of the known products of the prior art, cf. The results of the comparative tests collated in Table I below.

The novel products according to the invention are selected from the group consisting of:
(i) the β-D-phenylthioxylosides of the formula:

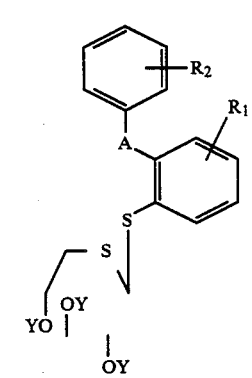

in which:
$R_1$ and $R_2$, which are identical or different, each represent a hydrogen atom, a trifluoromethyl group or a cyano group,
A represents the CHOH group or the CO group and
Y represents the hydrogen atom or an acyl group; and
(ii) epimers thereof when A is CHOH.

DETAILED DISCLOSURE OF THE INVENTION

The hydroxyl groups of the β-D-thioxylose residue are capable of being acylated, especially acetylated. The present invention therefore includes the derivatives of formula I in which the hydroxyl groups of the β-D-thioxylose residue are acylated, especially acetylated.

Among the acyl groups which are suitable according to the invention, there may be mentioned aliphatic groups which contain a total of 2 to 5 carbon atoms, the preferred acyl group being $CH_3CO$.

The compounds of formula I and the corresponding acylated compounds can be prepared according to a glycosidation reaction wherein:
(i) a compound of the formula:

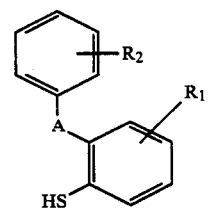

in which A, $R_1$ and $R_2$ are defined as above, is reacted with a thioxylose derivative selected from the group consisting of the halogenoacylthioxylosides and acylthioxylosides of the formulae:

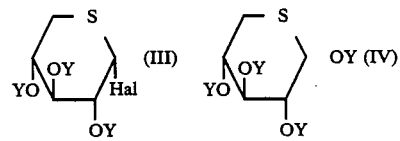

in which Hal represents a halogen atom, such as Cl or Br (the bromine atom being the preferred halogen atom here), and Y represents an acyl group, especially an aliphatic acyl group containing a total of 2 to 5 carbon atoms and preferably the acetyl group, in an inert solvent, at a rate of 1 mol of II to about 1.1 to 1.2 mol of thioxylose derivative, in the presence of an acid acceptor or a Lewis acid, and (ii) if necessary, a deacylation reaction is carried out at a temperature between room temperature (15°-25° C.) and the reflux temperature of the reaction medium in a $C_1$-$C_4$ lower alcohol (preferably methanol), in the presence of a metal alcoholate (preferably magnesium methylate or sodium methylate), to give a derivative of formula I in which Y is H.

In this method, it is important in stage (i) that the compound III is in the α configuration. On the other hand, the compound IV can be in the α or β configuration or a mixture of both configurations.

The acylated or non-acylated compounds of formula I in which A represents CHOH can also be obtained by reduction, according to a method known per se, of the compounds of formula I (acylated or non-acylated) in which A represents CO.

Again, the acylated or non-acylated compounds of formula I in which A represents CO can be obtained by oxidation, according to a method known per se, of the compounds of formula I (acylated or non-acylated) in which A represents CHOH.

The following are recommended among the glycosidation methods known to those skilled in the art:

the KOENIGS-KNORR method (described in "The Carbohydrates, Chemistry and Biochemistry", 2nd Edition, New York and London: Academic Press (1972), volume IA, pages 295-301); and the HELFERICH method (ibidem, pages 292-294).

The glycosidation reaction according to the invention will be carried out by one or other of these methods, the phenol being replaced with a thiophenol.

According to the best mode for carrying out the invention, it is recommended to condense 1 mol of the thiophenol II with about 1.1 to 1.2 mol of halogenoacyl-thioxyloside III in an inert solvent selected from polar and apolar solvents (for example dimethylformamide, tetrahydrofuran, dioxane, acetonitrile, nitromethane, benzene, toluene, xylenes and mixtures thereof), in the presence of mercuric cyanide.

It will be advantageous to use 2,3,4-tri-O-acetyl-1-bromo-α-D-5-thioxylopyranoside in a 1/1 (v:v) benzene/nitromethane mixture, in the presence of 1.1 to 1.3 mol of mercuric cyanide, at a temperature between 0° C. and the reflux temperature of the reaction medium, preferably at about 40°-50° C., for 1 to 4 hours, preferably for about 2 hours.

The glycosidation reaction leads in all cases to a mixture of the isomers of α and β configurations in variable proportions.

The isomer of β configuration is isolated by the methods known to those skilled in the art, for example by fractional crystallization or chromatography, especially flash chromatography [i.e. chromatography on a silica column under pressure according to the technique described by W. C. STILL et al. in J. Org. Chem. (1978), 42 (no. 14) 2923].

The reduction reactions which make it possible to obtain the acylated or non-acylated compounds of formula I in which A is CHOH from the corresponding compounds in which A is CO use conventional reagents such as metal hydrides, like $LiAlH_4$, $KBH_4$ or $NaBH_4$, in inert solvents such as ether, tetrahydrofuran or lower alcohols, especially methanol and ethanol, at a temperature between 0° C. and room temperature (15°-25° C.), for 1 to 12 hours, the preferred metal hydride being $NaBH_4$ and the reaction preferably being carried out in methanol at a temperature of 20° C.

If appropriate, the derivatives obtained are subjected to deacylation, more particularly deacetylation, which is carried out at a temperature between room temperature and the reflux temperature of the reaction medium, in a $C_1$-$C_4$ lower alcohol, in the presence of the corresponding metal alcoholate. Preferably, methanol will be chosen as the lower alcohol and sodium or magnesium methanolate as the metal alcoholate.

The deacylation and reduction reactions (in particular conversion of CO to CHOH) can optionally be carried out in succession without isolating the intermediate compound formed.

To obtain the thiophenols of formula II, it is recommended to:

(i) condense, in a strong basic medium, dimethylaminothiocarbamoyl chloride of the formula:

with a phenol of the formula:

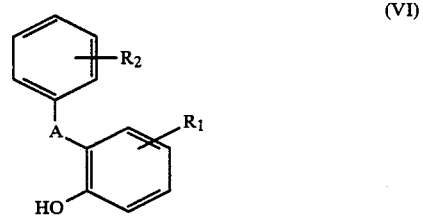

in which A, $R_1$ and $R_2$ have the meanings indicated above, to give a compound of the formula:

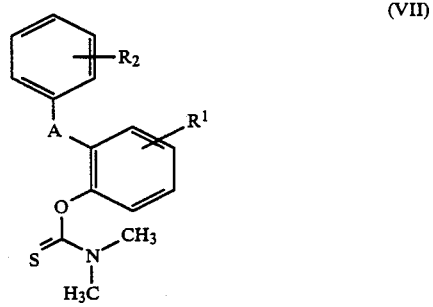

in which A, $R_1$ and $R_2$ have the meanings indicated above, (ii) subject the resulting compound of formula VII to a Newmann rearrangement (J. Org. Chem. (1966) 31, p. 3980), by heating, to give a compound of the formula:

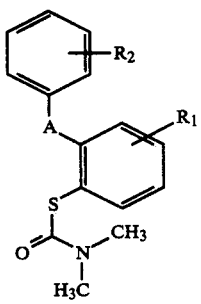

(VIII)

in which A, $R_1$ and $R_2$ have the meanings indicated above, and (iii) treat the resulting compound of formula VIII with a metal alcoholate, preferably sodium or magnesium methanolate, in a $C_1$–$C_4$ lower alcohol, preferably methanol, to give the thiophenol of formula II.

The compounds of formula II are novel compounds with the exception of the compounds in which $R_1$ and $R_2$ simultaneously represent the hydrogen atom.

The compounds of formula VI are novel compounds with the exception of the compounds in which $R_1$ represents the hydrogen atom when $R_2$ represents the hydrogen atom or the cyano group.

The compounds of formulae VII and VIII are novel compounds.

According to the invention, a therapeutic composition is proposed which contains, in association with a physiologically acceptable excipient, at least one compound selected from the group consisting of the products of formula I and epimers thereof. Of course, in a composition of this type, the active ingredient is present in a therapeutically effective amount.

The compounds of formula I are useful in therapy as antithrombotics. They are especially useful in the prevention and treatment of disorders of the venous circulation.

According to the invention, it is recommended to use a substance belonging to the group of compounds of formula I and epimers thereof in order to prepare an antithrombotic drug to be used in therapy for the treatment of disorders of the venous circulation.

Further characteristics and advantages of the invention will be understood more clearly from the following description of Preparative Examples, which in no way imply a limitation but are given by way of illustration, and of results of pharmacological tests.

PREPARATION I

Preparation of (2-benzoyl-4-cyanophenyl)-1,5-dithio-β-D-xylopyranoside

I (a) Preparation of O-(2-benzoyl-4-cyanophenyl) dimethylthiocarbamate 24 g (0.107 mol) of 3-benzoyl-4-hydroxybenzonitrile are dissolved in 240 cm³, of acetone, and 240 cm³ of water and 7.2 g (0.121 mol) of potassium hydroxide pellets are then added in succession. The mixture obtained is stirred for 15 minutes and a solution of 16.5 g (0.121 mol) of dimethylthiocarbamoyl chloride in 40 cm³ of acetone is then added. The emulsion obtained is then stirred for 3 hours at room temperature. The mixture obtained is decanted. After 200 cm³ of water have been added, the aqueous phase is extracted with ethyl acetate. The organic phases obtained are combined and then washed with a saturated solution of sodium chloride, dried over magnesium sulfate and evaporated under reduced pressure. Some of the product crystallizes spontaneously (23 g) and 8 g are then obtained after evaporation to dryness and washing with ether.

31 g of the expected product are finally obtained (yield: 90%).

Melting point=92° C.

I (b) Preparation of S-(2-benzoyl-4-cyanophenyl) dimethylthiocarbamate 10 g (0.032 mol) of the O-(2-benzoyl-4-cyanophenyl) dimethylthiocarbamate obtained in Preparation Ia are heated at 200° C. for 30 minutes under an argon atmosphere, with stirring.

10 g of the expected product are obtained in the form of an oil (yield: 100%).

$n_D^{28.5°\ C.}=1.6122$

I (c) Preparation of 3-benzoyl-4-mercaptobenzonitrile 10 g (0.032 mol) of the S-(2-benzoyl-4-cyanophenyl) dimethylthiocarbamate obtained in this way are dissolved in 100 cm³ of methanol. The green solution obtained is cooled to 0° C. and 19.3 cm³ of sodium methylate (8% w/v of Na in methanol) are added dropwise (the color turns red). The reaction medium is stirred for 3 hours at room temperature and then hydrolyzed with a 1N aqueous solution of hydrochloric acid. The expected product is extracted with ethyl acetate. A solution of sodium hydroxide is added to the organic phase obtained in this way and the aqueous phase is then acidified and extracted with ethyl acetate. The organic phase obtained is washed with a saturated solution of sodium chloride, dried over magnesium sulfate and evaporated under vacuum. The crystals obtained are washed with hexane and ether. 6 g of the expected product (yield: 80%) are obtained in the form of white crystals.

Melting Point=84° C.

I (d) Preparation of (2-benzoyl-4-cyanophenyl)-2,3,4-tri-O-acetyl-1,5-dithio-β-D-xylopyranoside (Example 1a)

8.16 g (0.024 mol) of 2,3,4-tri-O-acetyl-1-bromo-5-thio-β-D-xylopyranoside, 5 g (0.0205 mol) of the 3-benzoyl-4-mercaptobenzonitrile obtained in preparation Ic and 5.8 g (0.023 mol) of mercuric cyanide are added successively to a mixture of 125 cm³ of benzene and 125 cm³ of nitromethane on 20 g of a 0.4 nm molecular sieve (marketed by the company E. MERCK). The reaction medium obtained is stirred at room temperature for four hours and then filtered on Célite ® (i.e. diatomaceous silica for filtration). The residue is washed several times with ethyl acetate. The organic phase obtained is washed successively with a 1N solution of hydrochloric acid, a 1N solution of sodium hydroxide and a saturated solution of sodium chloride and then dried over magnesium sulfate and evaporated under reduced pressure. The oil obtained is purified by flash chromatography using a toluene/ethyl acetate mixture (8/2 v/v) as the eluent.

9 g of the expected product are obtained in the form of an oil (yield: 75%), which crystallizes on the addition of ether. The crystals obtained are recrystallized from ether.

5.38 g (yield: 46%) of the expected product are obtained.

Melting Point=173° C.

$[\alpha]_D^{20°\ C.}=+34.9°$ (c=0.53; $CHCl_3$)

I (e) Preparation of (2-benzoyl-4-cyanophenyl)-1,5-dithio-β-D-xylopyranoside (Example 1)

4 g (0.0078 mol) of the (2-benzoyl-4-cyanophenyl)-2,3,4-tri-O-acetyl-1,5-dithio-β-D-xylopyranoside obtained in Preparation Id are dissolved in 80 cm³ of methanol under an argon atmosphere. The solution obtained is cooled to 0° C. and 0.2 cm³ of sodium methylate (10% w/v solution of Na in methanol) is added. The mixture obtained is then stirred for one hour at room temperature and neutralized with Amberlite ® IR 120H+ resin. After filtration, the solvent is evaporated off under reduced pressure. 2.9 g of the expected product are obtained (yield: 70%).

Melting point=100° C.

$[\alpha]_D^{20° C.} = +72°$ (c=0.52; CH₃OH)

PREPARATION II

Preparation of (4-cyano-2-phenylhydroxymethylphenyl)-1,5-dithio-β-D-xylopyranoside (Example 2)

A mixture of 1 g (0.0026 mol) of the (2-benzoyl-4-cyanophenyl)-1,5-dithio-β-D-xylopyranoside obtained in Preparation Ie and 10 cm³ of methanol is cooled to 0° C. and 0.11 g (0.00284 mol) of NaBH₄ is then introduced. The resulting reaction mixture is stirred at 0° C. for 45 minutes and then neutralized by the addition of Amberlite ® IR 120H+ resin. After filtration, the solvent is evaporated off under reduced pressure. An amount of 1 g of the expected product (quantitative yield) is obtained after purification by flash chromatography using a chloroform/methanol mixture (95/5 v/v) as the eluent.

Melting Point=98°-100° C.

$[\alpha]_D^{20° C.} = +30.3°$ (c=0.52; CH₃OH)

PREPARATION III

Preparation of (2-benzoylphenyl)-1,5-dithio-β-D-xylopyranoside

III (a) Preparation of O-(2-benzoylphenyl) dimethylthiocarbamate

Following the procedure described in Preparation Ia and starting from 9.5 g (0.048 mol) of 2-hydroxyphenyl phenyl methanone and 10.3 g (0.083 mol) of dimethylthiocarbamoyl chloride, 11.2 g of the expected product are obtained (yield: 82%).

Melting point=98° C.

III (b) Preparation of S-(2-benzoylphenyl) dimethylthiocarbamate

Following the procedure described in Preparation Ib and starting from 9 g (0.031 mol) of the O-(2-benzoylphenyl) dimethylthiocarbamate obtained in Preparation IIIa, an amount of 1.8 g of the expected product is obtained in the form of an oil after purification by flash chromatography using a toluene/ethyl acetate mixture (98/2 v/v) as the eluent.

$n_D^{32° C.} = 1.6142$

III (c) Preparation of 2-mercaptophenyl phenyl methanone

Following the procedure described in Preparation Ic and starting from 1.8 g of S-(2-benzoylphenyl) dimethylthiocarbamate, 1 g of the expected product is obtained (yield: 74%).

III (d) Preparation of (2-benzoylphenyl)-2,3,4-tri-O-acetyl-1,5-dithio-β-D-xylopyyranoside (Example 3a)

Following the procedure described in Preparation Id and starting from 1.03 g (0.0048 mol) of 2-mercaptophenyl phenyl methanone, 1.29 g (0.0034 mol) of 2,3,4-tri-O-acetyl-1-bromo-5-dithio-E-D-xylopyranoside and 1.28 g (0.0051 mol) of mercuric cyanide, Hg(CN)₂, 0.16 g of the expected product (yield: 6%) is obtained after purification by flash chromatography using an ethyl acetate/toluene mixture (1/9 v/v) as the eluent.

Melting point=188° C.

$[\alpha]_D^{23° C.} = +34°$ (c=0.2; CH₃OH)

III (e) Preparation of (2-benzoylphenyl)-1,5-dithio-β-D-xylopyranoside (Example 3)

Following the procedure described in Preparation Ie and starting from 0.150 g (3.06.10⁻⁴ mol) of the (2-benzoylphenyl)-2,3,4-tri-O-acetyl-1,5-dithio-β-D-xylopyranoside obtained in Preparation IIIa and 2 ml of sodium methylate (8% w/v solution of Na in methanol), an amount of 0.090 g of the expected product (yield: 85%) is obtained after purification by flash chromatography using a methanol/chloroform mixture (5/95 v/v) as the eluent.

Melting point=82°-84° C.

$[\alpha]_D^{20° C.} 47.5°$ (c=0.225; CH₃OH)

PREPARATION IV

Preparation of (2-(4-cyanobenzoyl)phenyl)-1,5-dithio-β-D-xylopyranoside

IV (a) Preparation of 4-(2-methoxybenzoyl)benzonitrile 6.15 ml (0.049 mol) of 2-bromoanisole are added dropwise to 1.8 g (0.0074 mol) of magnesium in 3 ml of anhydrous tetrahydrofuran. After stirring for 20 minutes, the mixture solidifies. After dilution (addition of 20 ml of tetrahydrofuran), the resulting reaction medium is added dropwise to a mixture of 8.18 g (0.0494 mol) of 4-cyanobenzoyl chloride in 30 ml of anhydrous tetrahydrofuran, kept at −25° C. The reaction medium is then heated to room temperature and hydrolyzed with a concentrated hydrochloric acid/ice mixture and the expected product is extracted with an ethyl acetate/ether mixture. After precipitation by the addition of petroleum ether, 9.65 g (yield: 82%) of the expected product are obtained.

Melting point=92°-94° C.

IV (b) Preparation of 4-(2-hydroxybenzoyl)benzonitrile

A mixture of 6 g (0.0253 mol) of the 4-(2-methoxybenzoyl)benzonitrile obtained in Preparation IVa and 17.53 g (0.151 mol) of pyridinium chloride is heated for 12 hours at 220° C. The reaction medium is then hydrolyzed and the expected product is extracted with ethyl acetate. The organic phase is washed with a 1N aqueous solution of hydrochloric acid and a concentrated solution of NaCl and then dried over magnesium sulfate and the ethyl acetate is evaporated off under reduced pressure. An ethyl acetate/ether mixture is added to the oil obtained. The precipitate formed is removed and the filtrate is concentrated. After precipitation of the said filtrate with ether, 2.65 g of the expected product are obtained (yield: 47%).

Melting point=116° C.

IV (c) Preparation of O-2-(4-cyanobenzoyl)phenyl dimethylthiocarbamate 15 g (0.0672 mol) of the 4-(2-hydroxybenzoyl)benzonitrile obtained in Preparation IVb are suspended in a mixture of 150 cm³ of water and 100 cm³ of acetone, 4.15 g (0.0735 mol) of potassium hydroxide are then added and the resulting reaction mixture is stirred and heated for 20 minutes at 50° C. (a red coloration appears, followed by complete dissolution). The solution obtained is cooled to 0° C., a solution of 9.14 g (0.074 mol) of dimethylthiocarbamoyl chloride in 80 ml of acetone is added and the resulting mixture is stirred at room temperature for 3 hours. The reaction medium is hydrolyzed. The precipitate formed is filtered off and then triturated in ether. 17.4 g of the expected product are obtained in the form of a beige solid (yield: 84%).

Melting point=156°–157° C.

IV (d) Preparation of S-2-(4-cyanobenzoyl)phenyl dimethylthiocarbamate

Following the procedure described in Preparation Ib and starting from 2 g (0.0064 mol) of the O-2-(4-cyanobenzoyl)phenyl dimethylthiocarbamate obtained in Preparation IVc, 1.35 g of the expected product (yield: 45%) are obtained after purification by flash chromatography using a toluene/ethyl acetate mixture (99/1 v/v) as the eluent.

Melting point=102° C.

IV (e) Preparation of 4-(2-mercaptobenzoyl)benzonitrile

Following the procedure described in Preparation Ic and starting from 2.25 g (0.00725 mol) of O-2-(4-cyanobenzoyl)phenyl dimethylthiocarbamate, the expected product is obtained after purification by flash chromatography using an ethyl acetate/hexane mixture (1/6 v/v) as the eluent.

Melting point=98°–100° C.

IV (f) Preparation of (2-(4-cyanobenzoyl)phenyl)-2,3,4-tri-O-acetyl-1,5-dithio-$\beta$-D-xylopyranoside (Example 4a)

Following the procedure described in Preparation Id and starting from 1.54 g (0.00643 mol) of 4-(2-mercaptobenzoyl)benzonitrile, 3.7 g (0.010 mol) of 2,3,4-tri-O-acetyl-1-bromo-5-thio-$\alpha$-D-xylopyranoside and 2.526 g (0.010 mol) of mercuric cyanide, Hg(CN)$_2$, an amount of 0.4 g of the expected product (yield: 12%) is obtained after purification by flash chromatography using an ethyl acetate/toluene mixture (1/12 v/v) as the eluent, and then precipitation in methanol.

Melting point=160° C.

$[\alpha]_D^{22°\ C.} = -2.4°$ (c=0.5; CHCl$_3$)

IV (g) Preparation of (2-(4-cyanobenzoyl)phenyl)-1,5-dithio-$\beta$-D-xylopyranoside (Example 4)

Following the procedure described in Preparation Ie and starting from 0.36 g (0.00070 mol) of the (2-(4-cyanobenzoyl)phenyl)-2,3,4-tri-O-acetyl-1,5-dithio-$\beta$-D-xylopyranoside obtained in Preparation IVf, 0.170 g of the expected product (yield: 63%) is obtained after purification by flash chromatography using a methanol/chloroform mixture (1/25 v/v) as the eluent, and then precipitation in methanol.

Melting point=154°–155° C.

$[\alpha]_D^{20°\ C.} = +33.4°$ (c=0.1; CH$_3$OH)

PREPARATION V

Preparation of (2-(4-cyanophenylhydroxymethyl)phenyl)-1,5-dithio-$\beta$-D-xylopyranoside (Example 5)

0.2 ml of sodium methylate (8% w/v of Na in methanol) is added to a solution of 450 mg (0.00087 mol) of (2-(4-cyanobenzoyl)phenyl)-2,3,4-tri-O-acetyl-1,5-dithio-$\beta$-D-xylopyranoside in 5 ml of methanol. The progress of the deacetylation is followed by chromatography using a chloroform/ethanol mixture (9/1 v/v) as the eluent. When the deacetylation is complete, 0.050 g (0.0013 mol) of sodium borohydride (NaBH$_4$) is added to the reaction medium at 0° C. The resulting mixture is neutralized by the addition of Amberlite IR 120H$^+$ resin. After filtration, the solvent is evaporated off under reduced pressure to give 0.065 g of the expected product.

Melting point=85°–95° C. $[\alpha]_D^{20°\ C.} = +12.5°$ (c=0.12; CHCl$_3$)

PREPARATION VI

Preparation of (2-(3-cyanobenzoyl)phenyl)-1,5-dithio-$\alpha$-D-xylopyranoside

VI (a) Preparation of 3-(2-methoxybenzoyl)benzonitrile 30 g (0.16 mol) of 2-bromoanisole are added dropwise to a mixture of 3.85 g (0.16 mol) of magnesium, containing a crystal of iodine, in 75 ml of anhydrous tetrahydrofuran and the reaction mixture is then refluxed for 1 hour. The resulting solution is then added dropwise to a solution of 26.48 g (0.16 mol) of 3-cyanobenzoyl chloride in 75 ml of anhydrous tetrahydrofuran, cooled to $-75°$ C. The temperature is allowed to rise to 20° C., the reaction medium is hydrolyzed with a 1N aqueous solution of hydrochloric acid and the expected product is then extracted with ethyl acetate. The organic phase obtained is washed with water, dried over magnesium sulfate and then evaporated under reduced pressure. 30 g of the expected product (yield: 80%) are obtained in the form of crystals.

Melting point=180° C.

VI (b) Preparation of 3-(2-hydroxybenzoyl)benzonitrile

A mixture of 16 g (0.0675 mol) of 3-(2-methoxybenzoyl)benzonitrile and 50 g (0.43 mol) of pyridinium chloride is heated at 180° C. for 12 hours and the reaction mixture is then cooled to 140° C. and hydrolyzed with an ice/concentrated hydrochloric acid mixture. After stirring for 15 minutes, the expected product is extracted with ethyl acetate. The organic phase obtained is washed with water and then brine (saturated aqueous solution of NaCl) until the pH is neutral, dried over magnesium sulfate and then evaporated under reduced pressure. The resulting oil is purified on silica using a toluene/ethyl acetate mixture as the eluent. After evaporation of the solvents from the eluate, 8.5 g of a yellow solid are obtained (yield: 60%).

Melting Point=100° C.

VI (c) Preparation of O-2-(3-cyanobenzoyl)phenyl dimethylthiocarbamate

Following the procedure described in Preparation Ia and starting from 8.5 g (0.038 mol) of the 3-(2-hydroxybenzoyl)benzonitrile obtained in Preparation VIb, 2.56 g (0.046 mol) of potassium hydroxide and 5.65 g (0.046 mol) of dimethylthiocarbamoyl chloride, 11 g of the expected product are obtained (yield: 94%).

Melting point=90° C.

VI (d) preparation of S-2-(3-cyanobenzoyl)phenyl dimethylthiocarbamate

Following the procedure described in Preparation Ib and starting from 7 g (0.0226 mol) of the O-2-(3cyanobenzoyl)phenyl dimethylthiocarbamate obtained in Preparation VIc, an amount of 4.2 g of the expected product (yield: 60%) is obtained after purification by flash chromatography using a toluene/ethyl acetate mixture (90/2 v/v) as the eluent.

Melting point=86° C.

VI (e) Preparation of 3-(2-mercaptobenzoyl)benzonitrile

Following the procedure described in Preparation Ic and starting from 3.3 g (0.0106 mol) of the S-2-(3-cyanobenzoyl)phenyl dimethylthiocarbamate obtained in Preparation VId, an amount of 1.29 g of the expected product (yield: 51%), characterized by NMR, is obtained after Purification by chromatography on a silica column using a toluene/ethyl acetate mixture (85/15 v/v) as the eluent.

VI (f) Preparation of (2-(3-cyanobenzoyl)phenyl)-2,3,4-tri-O-acetyl-1,5-dithio-β-D-xylopyranoside (Example 6a)

Following the procedure described in Preparation Id and starting from 0.300 g (0.0012 mol) of the 3-(2-mercaptobenzoyl)benzonitrile obtained in Preparation VIe, an amount of 0.200 g of the expected product (yield: 35%) is obtained after purification by flash chromatography using a toluene/ethyl acetate mixture (8/2 v/v) as the eluent, and then crystallization from ethyl ether.

Melting point=140° C.
$[\alpha]_D^{20°\ C.} = +21°$ (c=24; CH$_3$OH)

VI (g) Preparation of (2-(3-cyanobenzoyl)phenyl)-1,5-dithio-β-D-xylopyranoside (Example 6)

Following the procedure described in Preparation Ie and starting from 0.200 g (0.00039 mol) of the (2-(3-cyanobenzoyl)phenyl)-2,3,4-tri-O-acetyl-1,5-dithio-β-D-xylopyranoside obtained in Preparation VIf, an amount of 0.105 g (yield: 70%) of the expected product is obtained after purification by flash chromatography using a chloroform/methanol mixture (95/5 v/v) as the eluent.

Melting point=70°-83° C.
$[\alpha]_D^{20°\ C.} = +25.16°$ (c=0.15; CH$_3$OH)

PREPARATION VII

Preparation of (2-(3-cyanophenylhydroxymethyl)phenyl)-1,5-dithio-β-D-xylopyranoside (Example 7)

Following the procedure described in Preparation II and starting from 0.170 g (0.00033 mol) of the (2-(3-cyanobenzoyl)phenyl)-1,5-dithio-β-D-xylopyranoside obtained in Preparation VIg, 0.070 g of the expected product (yield: 60%) is obtained after purification by flash chromatography using a chloroform/methanol mixture as the eluent.

Melting Point=57°-80° C.
$[\alpha]_D^{22°\ C.} = +38.3°$ (c=0.1; CH$_3$OH)

PREPARATION VIII

Preparation of (2-(2-cyanobenzoyl)phenyl)-1,5-dithio-β-D-xylopyranoside

VIII (a) Preparation of 2-bromophenyl 2-methoxyphenyl methanone

Following the Procedure described in Preparation VIa and starting from 9.4 g (0.050 mol) of 2-bromoanisole, 1.7 g (0.069 mol) of magnesium and 11 g (0.050 mol) of 2-bromobenzoyl chloride, 9.6 g of the expected product (yield: 66%) are obtained after crystallization from ether.

Melting Point=68° C.

VIII (b) preparation of 2-bromophenyl 2-hydroxyphenyl methanone

A mixture of 21 g (0.072 mol) of the 2-bromophenyl 2-methoxyphenyl methanone obtained in Preparation VIIIa, 50 ml of a 30% aqueous solution of hydrobromic acid and 50 ml of acetic acid is refluxed for 4 hours. The reaction mixture is hydrolyzed with ice and then extracted with ethyl acetate. The organic phase is washed with water until the pH is neutral and then evaporated under vacuum. 6.4 g of the expected product (yield: 85%) are obtained after crystallization from diisopropyl ether.

Melting Point=78° C.

VIII (c) Preparation of 2-(2-hydroxybenzoyl)benzonitrile

A mixture of 10.1 g (0.036 mol) of 2-bromophenyl 2-hydroxyphenyl methanone and 6.6 g (0.074 mol) of cuprous cyanide (CuCN) is heated at 180° C. for 2 hours. The resulting reaction medium is hydrolyzed with a 1N hydrochloric acid/ice mixture (50/100 v/v) and then extracted with ethyl acetate. The organic phase obtained is washed with a 1N aqueous solution of hydrochloric acid, then a saturated aqueous solution of NaCl and then water until the pH is neutral, after which it is evaporated under reduced pressure. An amount of 5.8 g of the expected product (yield: 59%) is obtained after purification by flash chromatography using a hexane/ethyl acetate mixture (5/1 v/v) as the eluent.

Melting point=100° C.

VIII (d) Preparation of O-2-(2-cyanobenzoyl)phenyl dimethylthiocarbamate 1 g (0.041 mol) of sodium hydride is added in small amounts to a solution of 6.7 g (0.030 mol) of the 2-(2-hydroxybenzoyl)benzonitrile obtained in Preparation VIIIc in 200 ml of tetrahydrofuran. The mixture obtained is stirred for 1 hour at 50° C. The reaction medium is cooled to room temperature and a solution of 4.6 g (0.037 mol) of dimethylthiocarbamoyl chloride in 50 ml of tetrahydrofuran is added. The mixture obtained is stirred for 3 hours at room temperature and then hydrolyzed with an ice/water mixture. Extraction is carried out with ethyl acetate. The organic phase obtained is washed with water, dried over magnesium sulfate and then evaporated under reduced pressure. 6 g of the expected product (yield: 64.5%) are obtained after crystallization from ether.

Melting point=140° C.

VIII (e) Preparation of S-2-(2-cyanobenzoyl)phenyl dimethylthiocarbamate

Following the procedure described In Preparation Ib and starting from 6.5 g (0.021 mol) of the O-2-(2-cyanobenzoyl)phenyl dimethylthiocarbamate obtained in Preparation VIIId, an amount of 4.65 g of the expected product (yield: 68.5%) is obtained after purification by flash chromatography using a toluene/ethyl acetate mixture (6/1 v/v) as the eluent, and crystallization from an ethyl acetate/ether mixture.

Melting point=130° C.

VIII (f) Preparation of 2-(2-mercaptobenzoyl)benzonitrile

Following the procedure described in Preparation Ic and starting from 1 g (0.0032 mol) of the S-2-(2cyanobenzoyl)phenyl dimethylthiocarbamate obtained in Preparation VIIIe, 1.2 g of the expected product (yield: 54.5%) are obtained after purification by flash chromatography.

Melting point=94° C.

VIII (g) Preparation of (2-(2-cyanobenzoyl)phenyl)-2,3,4-tri-O-acetyl-1,5-dithio-β-D-xylopyranoside (Example 8a)

Following the procedure described in Preparation Id and starting from 1.2 g (0.0050 mol) of 2-(2mercaptobenzoyl)benzonitrile, 2.14 g (0.0060 mol) of 2,3,4-tri-O-acetyl-1-bromo-5-thio-α-D-xylopyranoside and 1.27 g (0.0050 mol) of mercuric cyanide (Hg(CN)$_2$), 1.4 g of the expected product (yield: 54.5%) are obtained after crystallization from ether.

Melting point=210° C.

$[\alpha]_D^{20°\ C.} = +51.4°$ (c=0.3; CH$_3$OH)

VIII (h) Preparation of (2-(2-cyanobenzoyl)phenyl)-1,5-dithio-β-D-xylopyranoside (Example 8)

Following the procedure described in Preparation Ie and starting from 0.500 g (0.00097 mol) of the (2-(2-cyanobenzoyl)phenyl)-2,3,4-tri-O-acetyl-1,5-dithio-β-D-xylopyranoside obtained in Preparation VIIIg, an amount of 0.250 g of the expected product (yield: 70%) is obtained after crystallization from ether.

Melting Point=107°-112° C.

$[\alpha]_D^{20°\ C.} = +32.5°$ (c=0.36; CH$_3$OH)

PREPARATION IX

Preparation of (2-(4-cyanobenzoyl)-4-trifluoromethylphenyl)-1,5-dithio-β-D-xylopyranoside IX (a) Preparation of 4-(2-methoxy-5-trifluoromethylbenzoyl)benzonitrile Following the procedure described in Preparation IVa and starting from 1.85 g (0.076 mol) of 2-bromo-4-trifluorometbylanisole, 1.86 g (0.0765 mol) of magnesium and 8.45 g (0.051 mol) of 4-cyanobenzoyl chloride, an amount of 12 g (yield: 77.5%) of the expected product is obtained after purification by flash chromatography using a toluene/ethyl acetate mixture (8/1 v/v) as the eluent.

Melting point=88° C.

IX (b) Preparation of 4-(2-hydroxy-5-trifluoromethylbenzoyl)benzonitrile

Following the procedure described in Preparation IVb and starting from 13.5 g (0.049 mol) of 4-(2-methoxy-5-trifluoromethylbenzoyl)benzonitrile and 31 g (0.27 mol) of pyridinium chloride, an amount of 8.4 g of the expected product (yield: 65%) is obtained after purification by flash chromatography using a hexane/ethyl acetate mixture (5/1 v/v) as the eluent.

Melting point=118° C.

IX (c) Preparation of O-2-(4-cyanobenzoyl)-4-trifluoromethylphenyl dimethylthiocarbamate Following the procedure described in Preparation IVc and starting from 8 g (0.0274 mol) of 4-(2-hydroxy-5-trifluoromethylbenzoyl)benzonitrile, 1.97 g (0.035 mol) of potassium hydroxide and 4.1 g (0.033 mol) of dimethylthiocarbamoyl chloride, an amount of 8.1 g of the expected product (yield: 77.9%) is obtained after purification by flash chromatography using a hexane/ethyl acetate mixture (5/1 v/v) as the eluent.

Melting point=142° C.

IX (d) Preparation of S-2-(4-cyanobenzoyl)-4-trifluoromethylphenyl dimethylthiocarbamate Following the procedure described in Preparation IVd and starting from 7.9 g (0.0185 mol) of O-2-(4-cyanobenzoyl)-4-trifluoromethylphenyl dimethylthiocarbamate, an amount of 6.7 g of the expected product (yield: 85%) is obtained after crystallization from diisopropyl ether.

Melting point=159° C.

IX (e) Preparation of 4-(2-mercapto-5-trifluoromethylbenzoyl)benzonitrile

Following the procedure described in Preparation IVe and starting from 6.1 g (0.016 mol) of the S-2-(4-cyanobenzoyl)-4-trifluoromethylphenyl dimethylthiocarbamate obtained in Preparation IXd, an amount of 3.3 g (yield 67%) of the expected product, characterized by NMR, is obtained after purification by flash chromatography using a toluene/ethyl acetate mixture (9/1 v/v) as the eluent.

IX (f) Preparation of (2-(4-cyanobenzoyl)-4-trifluoromethylphenyl)-2,3,4-tri-O-acetyl-1,5-dithio-β-D-xylopyranoside (Example 9a)

Following the procedure described in Preparation Id and starting from 3 g (0.0097 mol) of the 4-(2-mercapto-5-trifluoromethylbenzoyl)benzonitrile obtained in Preparation IXe, 4.2 g (0.012 mol) of 2,3,4-tri-O-acetyl-1-bromo-5-thio-α-D-xylopyranoside and 2.5 g (0.0099 mol) of mercuric cyanide (Hg(CN)$_2$), an amount of 1.3 g of the expected product (yield: 22%) is obtained after crystallization from ether.

Melting point=210° C.

$[\alpha]_D^{20°\ C.} = +6°$ C. (c=25; CHCl$_3$)

IX (g) preparation of (2-(4-cyanobenzoyl)-4-trifluoromethylphenyl)-1,5-dithio-β-D-xylopyranoside (Example 9)

Following the procedure described in Preparation Ie and starting from the (2-(4-cyanobenzoyl)-4-trifluoromethylphenyl)-2,3,4-tri-O-acetyl-1,5-dithio-β-D-xylopyranoside obtained in Preparation IXf, an amount of 0.45 g (yield: 56%) of the expected product is obtained after purification by flash chromatography using a methylene chloride/ethyl acetate mixture (8/2 v/v) as the eluent.

Melting point=106°-111° C.

$[\alpha]_D^{20°\ C.} = +39.8°$ (c=0.63: CH$_3$OH)

PREPARATION X

Preparation of (2-(4-cyanophenylhydroxymethyl)-4-trifluoromethylphenyl)-1,5-dithio-β-D-xylopyranoside (Example 10)

Following the procedure described in Preparation II and starting from 0.24 g (0.000527 mol) of the (2-(4-cyanobenzoyl)-4-trifluoromethylphenyl)-1,5-dithio-β-D-xylopyranoside obtained in Preparation IXg and 0.022 g (0.000579 mol) of NaBH$_4$, an amount of 0.2 g (yield: 83%) of the expected product is obtained after purification by flash chromatography using a chloroform/methanol mixture (95/5 v/v) as the eluent.

Melting point=76°-87° C.

$[\alpha]_D^{20°\ C.} = +42.8°$ (c=0.25; CH$_3$OH)

The antithrombotic activity of the products according to the invention was demonstrated by the following protocol for venous thrombosis:

A venous stasis is produced under hypercoagulation according to the technique described by WESSLER et al. (J. Applied Physiol. 1959, p. 943-946). As in the technique described by J. HAUPMAN et al. (Thrombosis and Haemostasis 43 (2) 1980, p. 118), the hypercoagulant used is a solution of activated factor X (Xa) supplied by the company Flow Laboratories (71 Knat per 12.5 ml of physiological serum).

The study is performed on unfasted male Wistar rats weighing 250 to 280 g and divided up into groups of 10 animals each. The test products are administered orally as a suspension in PEG 400. A thrombosis is induced 4 hours after this treatment and the thrombus formed is removed and weighed.

The results obtained at a dose of 12.5 mg/kg p.o. have been collated in Table I. The results obtained with the known products of the above-mentioned prior art have also been collated in this Table.

The venous antithrombotic activity of the products according to the invention is distinctly superior to the activity of the known products of the prior art.

TABLE I

| EXAMPLE | % INHIBITION |
| --- | --- |
| 1 | 69 |
| 1a | 43.8 |
| 2 | 61 |
| 3 | 4 |
| 4 | 88 |
| 5 | 62 |
| 6 | 59 |
| 7 | 54 |
| 8 | 57 |
| 9 | 56.5 |
| 10 | 61 |
| A | 14 |
| B | 5.5 |

Notes:

A: comparison product described in Example 1 of European patent document A-0133 103

B: comparison product described in Example 97 of European patent document B-0051 023

What is claimed is:

1. An oside compound selected from the group consisting of:

(i) the β-D-phenylthioxylosides of the formula:

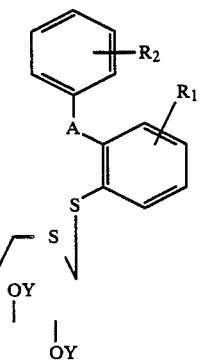 (I)

in which:

$R_1$ and $R_2$, which are identical or different, each represent a hydrogen atom, a trifluoromethyl group or a cyano group, A represents the CHOH group or the CO group and Y represents the hydrogen atom or an alkanoyl radical containing from 2 to 5 carbon atoms group; and (ii) epimers thereof when A is CHOH.

2. An oside compound according to claim 1 in which the acyl group Y is aliphatic, contains from 2 to 5 carbon atoms and represents the $CH_3CO$ group.

3. A therapeutic composition comprising, in association with a physiologically acceptable excipient, at least one oside compound selected from the group consisting of the β-D-phenylthioxylosides of formula I and epimers thereof.

4. A method of treating the venous circulatory system, which comprises administering, to a patient in need of such a treatment, an antithrombotic effect amount of at least one substance selected from the group consisting of the β-D-phenylthioxyloside compounds of formula I and epimers thereof according to claim 1.

* * * * *